US00PP22674P2

(12) United States Plant Patent
Kennedy

(10) Patent No.: US PP22,674 P2
(45) Date of Patent: Apr. 17, 2012

(54) ***PRIMULA* PLANT NAMED 'K 74'**

(50) Latin Name: *Primula acaulis*
Varietal Denomination: K 74

(76) Inventor: Joseph Olivier Kennedy, Ballycastle (IE)

( * ) Notice: Subject to any disclaimer, the term of this patent is extended or adjusted under 35 U.S.C. 154(b) by 0 days.

(21) Appl. No.: 12/932,944

(22) Filed: Mar. 10, 2011

(51) Int. Cl.
*A01H 5/00* (2006.01)

(52) U.S. Cl. ..... Plt./472

(58) Field of Classification Search ..... Plt./472
See application file for complete search history.

*Primary Examiner* — Kent L Bell
(74) *Attorney, Agent, or Firm* — Penny J. Aguirre

(57) ABSTRACT

A new cultivar of *Primula* plant, 'K 74', characterized by its foliage that is a blend of dark green and bronze, its large flowers that are white in color, its relatively vigorous growth habit, and its healthy foliage that has been observed to be disease resistant.

2 Drawing Sheets

Botanical classification: *Primula acaulis*.
Variety denomination: 'K 74'.

CROSS REFERENCE TO A RELATED APPLICATION

This application is co-pending with a U.S. Plant Patent Application filed for a plant derived from the same cross in the Inventor's breeding program that is entitled *Primula* Plant Named 'K 72' (U.S. Plant patent application Ser. No. 12,932,961).

BACKGROUND OF THE INVENTION

The present invention relates to a new and distinct cultivar of *Primula* plant, botanically known as *Primula* 'K 74' and will be referred to hereinafter by its cultivar name, 'K 74'. The new cultivar of *Primula* is a hardy herbaceous perennial grown for landscape use.

The new cultivar was derived from a controlled breeding program conducted by the Inventor at his nursery in Ballycastle, Northern Ireland. The overall purpose of the breeding program that was established in the 1980s is to make selections of *Primula* plants with unique and improved characteristics to plants from the 'Garryard' family of primroses, a group of *Primula* cultivars that emerged in the 1950s and had the common characteristic of having bronze colored foliage.

'K 74' was selected in the Inventor's greenhouse in 2006 as a single unique plant from amongst the seedlings derived from a cross made in 2003 between two unnamed plants of *Primula acaulis* from the Inventor's breeding program as the parents.

Asexual reproduction of the new cultivar was first accomplished by in vitro propagation in 2009 under the direction of the Inventor in Ballycastle, Northern Ireland. Asexual propagation has determined the characteristics to be stable and reproduced true to type in successive generations.

SUMMARY OF THE INVENTION

The following traits have been repeatedly observed and are determined to be the characteristics of the new cultivar. These attributes in combination distinguish 'K 74' as a unique cultivar of *Primula*.

1. 'K 74' exhibits foliage that is a blend of dark green and bronze.
2. 'K 74' exhibits large flowers that are white in color.
3. 'K 74' exhibits a vigorous growth habit for a dark foliaged cultivar of *Primula*.
4. 'K 74' exhibits healthy foliage that has been observed to be disease resistant.

In comparison to its parent plants, 'K 74' is more vigorous and has better bronzing to the foliage and has flowers that are larger and clearer white in color. 'K 74' can be most closely compared to the cultivar 'K 72' from the same breeding program. 'K 72' is similar to 'K 74' in having good vigor and large flowers, however 'K 72' differs in having slightly more bronzing to the foliage and in having red flowers. 'K 74' can also be compared to the cultivar 'Garryard' (syns. 'Garryard Guinever', 'Guinever'), not patented. 'Garryard' differs from 'K 74' in having foliage that is less bronze in color and in having flowers that are smaller in size and pink in color.

BRIEF DESCRIPTION OF THE DRAWINGS

The accompanying colored photographs illustrate the overall appearance and distinct characteristics of the new *Primula*. The plant in the photograph is 6 months in age as grown in a 10.5-cm container in a cold-storey greenhouse in The Netherlands.

The photograph in FIG. 1 provides a side view of 'K 74' in bloom.

Figure 1:
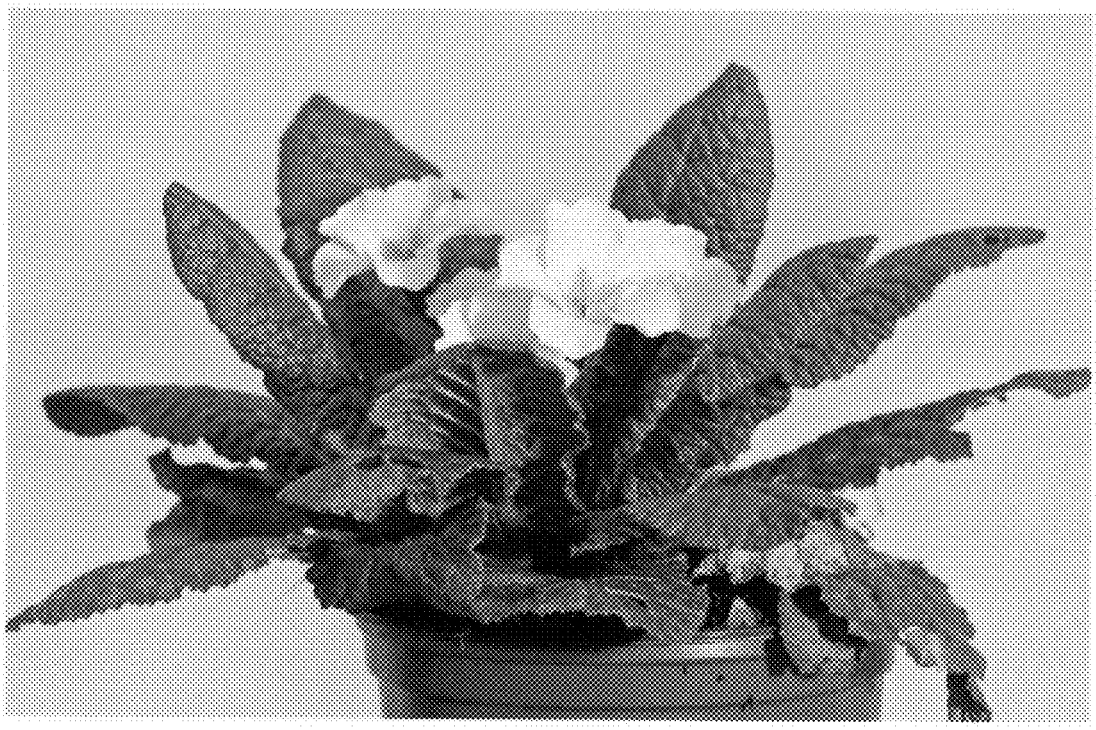
Figure 2:
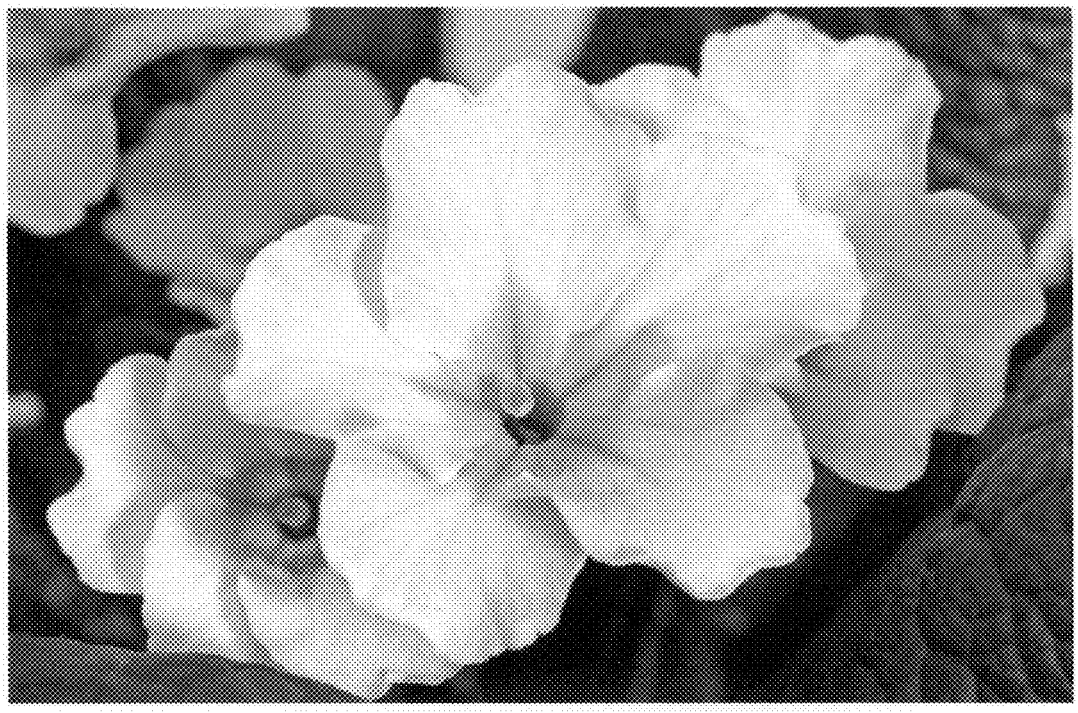

The photograph in FIG. 2 provides a close-up view of a flower of 'K 74'.

Figure 3:
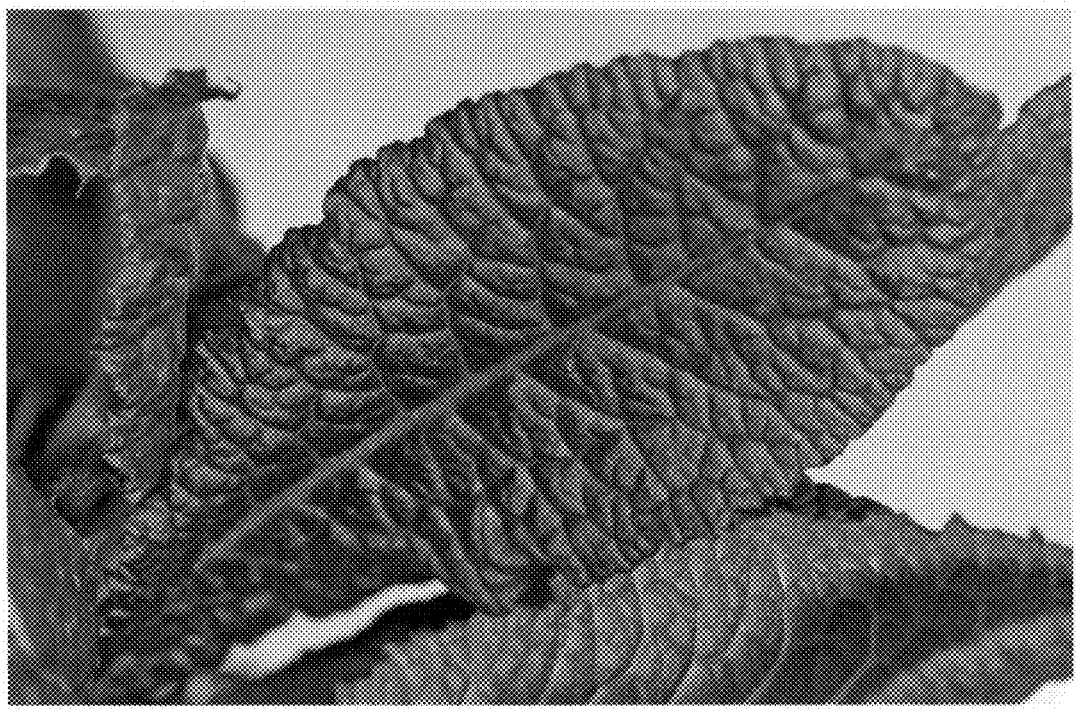

The photograph in FIG. 3 provides a close-up view of the foliage of 'K 74'.

The colors in the photograph may differ slightly from the color values cited in the detailed botanical description, which accurately describe the colors of the new *Primula*.

DETAILED BOTANICAL DESCRIPTION

The following is a detailed description of six month-old plants of the new cultivar as grown in 10.5-cm containers in a cold-storey greenhouse in The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Typically March to May in Ballycastle, The Netherlands.

*Plant habit.*—Herbaceous perennial, clump-forming, tight rosette.

*Height and spread.*—Reaches about 20 cm in height and about 35 cm in width.

*Cold hardiness.*—Observed to be hardy to −10° C. in western Europe.

*Diseases.*—Observed to be disease resistant under the conditions tested.

*Root description.*—Fibrous roots.

*Branching habit.*—Basal rosettes.

*Propagation.*—Tissue culture preferred.

*Growth habit.*—Vigorous for a bronzed foliaged cultivar of *Primula*.

Foliage description:

*Leaf shape.*—Oblanceolate.

*Leaf division.*—Simple.

*Leaf base.*—Broad cuneate.

*Leaf apex.*—Rounded.

*Leaf venation.*—Pinnate, on upper surface; 148B to 148C in color fading towards the base into 182B to 182C, lower surface; 148D in color fading towards the base into 182D, sparsely pubescent on main veins, secondary veins and tertiary veins with thin and soft hairs, average length 0.75 mm, 156D to 157D in color.

*Leaf margins.*—Crenulate, finely sinuate.

*Leaf arrangement.*—*Rosette.*

*Leaf surface.*—Rugose to bullate and moderately glossy, finely pubescent on lower surface.

*Leaf color.*—Newly emerged foliage, upper surface; 146A to 147A, newly emerged foliage, lower surface; 148A, mature foliage, upper surface; 147A, mature foliage, lower surface; 148A.

*Leaf size.*—About 11.4 cm in length and 4.4 cm in width.

*Leaf quantity.*—Average of 24 per rosette.

*Leaf attachment.*—Sessile.

Inflorescence description:

*Inflorescence type.*—Funnel form, lower 50% fused into a tube, rosette formed flowers.

*Flower number.*—Average of 5 per rosette.

*Flower fragrance.*—None.

*Flower aspect.*—Upright to slightly outward.

*Flower longevity.*—About 10 days, depending on temperature and sunlight exposure.

*Flower type.*—Single.

*Flower size.*—Average of 3.5 cm in diameter and 2.8 cm in depth.

*Flower buds.*—Elliptic in shape, average of 8 flower buds per rosette, average of 1.4 cm in length and 5 mm in diameter, color; 145A to 145B then fading to top and turning into 178A, flower buds ribbed (5 ribs); 184D.

*Sepals.*—5, Narrow oblong, lower 55% fused, margin entire, average of 2 cm in length and 3 mm in width, acuminate apex, fused base, fused arrangement into a campanulate calyx with upper 45% free, surface is dull, main vein moderately pubescent with short soft hairs, average length of hairs 1 mm, color; N155B, color: young and mature upper surface; 146C, tinged at the tip with 176B to 176C, young lower surface; 145A to 145B, top 178A, main vein 184D, mature lower surface; 148A, top 178A, main vein 184D.

*Petals.*—An average of 5 per flower, rotate arrangement, spathulate, free upper 50% of the petals orbicular, surface is slightly glossy and slightly velvety, smooth texture, upper part of the tube on the lower surface is sparsely pubescent with very short hairs with an average length of 0.3 mm, 149D to 150D in color, margin sinuate, base cuneate, apex is rounded, average of 3.3 cm in length and 1.8 cm in width, color: opening flowers upper surface; NN155D, veined 73D, base ("eye") 9A to 12A, tube 150A to 150B, fully opened flowers upper surface; N155C to N155D, veined 73D, base ("eye") 9A to 12A, tube 150A to 150B, opening and fully opened flowers lower surface; NN155D, veined 73D, tube 150B to 150C.

*Peduncle.*—Average of 2 mm in diameter and 6 cm in length, moderate strength, 186A to 186B in color, glabrous surface.

*Pedicel.*—None.

Reproductive organs:

*Pistils.*—About 1 per flower, average of 1.6 cm in length, club shaped stigma N144A in color, style is an average of 1.5 cm in length and 145C and strongly tinged 170C in color, and ovary is 145A to 145B in color.

*Stamens.*—Average 5, no filaments present, anthers are basifixed and oblong in shape, average of 2 mm in diameter, and N200A in color, pollen is moderate in quantity and 11A in color.

*Fruit.*—Fruit and seed production was not observed under the conditions tested.

It is claimed:

1. A new and distinct variety of *Primula* plant named 'K 74' as described and illustrated herein.

* * * * *